(12) United States Patent
Böttcher et al.

(10) Patent No.: US 6,464,954 B2
(45) Date of Patent: Oct. 15, 2002

(54) METHOD FOR HYDROGENATING AN ANTHRAQUINONE COMPOUND

(75) Inventors: Arnd Böttcher, Frankenthal; Jochem Henkelmann, Mannheim; Franz Josef Bröcker, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,404

(22) PCT Filed: Oct. 26, 1998

(86) PCT No.: PCT/EP98/06789

§ 371 (c)(1),
(2), (4) Date: Apr. 26, 2000

(87) PCT Pub. No.: WO99/21792

PCT Pub. Date: May 6, 1999

(65) Prior Publication Data

US 2002/0012627 A1 Jan. 31, 2002

(30) Foreign Application Priority Data

Oct. 27, 1997 (DE) .......................... 197 47 407

(51) Int. Cl.⁷ ...................... C01B 15/023; C07C 50/18

(52) U.S. Cl. ...................... 423/588; 423/590; 552/208

(58) Field of Search ................... 423/588, 590; 552/208

(56) References Cited

U.S. PATENT DOCUMENTS

| | | | | |
|---|---|---|---|---|
| 3,030,186 A | * | 4/1962 | Kreuz et al. ............. | 423/588 |
| 3,615,207 A | * | 10/1971 | Lee ............. | 423/588 |
| 3,887,490 A | * | 6/1975 | Schreyer et al. ............. | 423/588 |
| 4,258,025 A | * | 3/1981 | Copelin ............. | 423/588 |
| 4,336,241 A | * | 6/1982 | Diamond et al. ............. | 423/588 |
| 4,800,075 A | * | 1/1989 | Jenkins ............. | 423/588 |
| 5,772,977 A | * | 6/1998 | Jenkins et al. ............. | 423/588 |

FOREIGN PATENT DOCUMENTS

EP 102934 * 3/1984

\* cited by examiner

*Primary Examiner*—Wayne A. Langel
(74) *Attorney, Agent, or Firm*—Oblon, Spivak, McClelland, Maier & Neustadt, P.C.

(57) ABSTRACT

A process for hydrogenating an anthraquinone compound or a mixture of two or more thereof utilizes specific catalysts comprising, as active metal, a metal of transition group VIII of the Periodic Table of the Elements.

18 Claims, No Drawings

METHOD FOR HYDROGENATING AN ANTHRAQUINONE COMPOUND

The present invention relates to a process for hydrogenating an anthraquinone compound or a mixture of two or more thereof by contacting the anthraquinone compound or the mixture of two or more thereof with a catalyst comprising, as active metal, at least one metal of transition group VIII of the Periodic Table of the Elements and a process for preparing hydrogen peroxide by the anthraquinone process comprising a hydrogenation step as defined above and the reaction of the anthraquinone compound obtained in this step with an oxygen-containing gas.

Virtually all of the hydrogen peroxide produced worldwide is prepared by the anthraquinone process.

The process is based on the catalytic hydrogenation of an anthraquinone compound to give the corresponding anthrahydroquinone compound followed by reacting the latter with oxygen to give hydrogen peroxide and subsequently removing the hydrogen peroxide formed by extraction. The catalyst cycle is closed by rehydrogenation of the reformed anthraquinone compound.

The basic reactions are summarized in the scheme below:

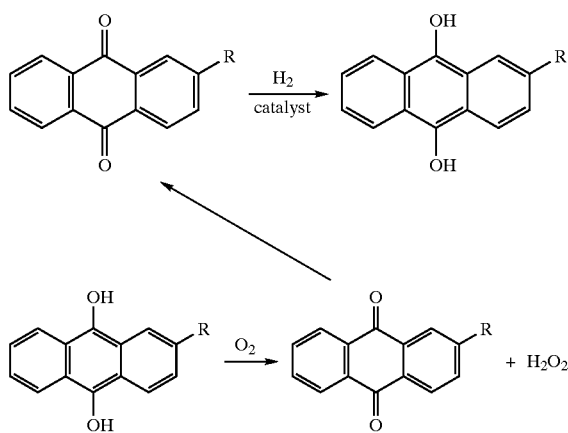

The anthraquinone compounds used are typically dissolved in a mixture of several organic solvents. The resulting solution is referred to as the working solution. In the anthraquinone process, this working solution is usually passed through the above-described process steps in a continuous manner.

The anthraquinone process is reviewed in Ullmann's Encyclopedia of Industrial Chemistry, 5th ed., vol. A13, pp. 447–456.

A particularly important step of the anthraquinone process is the hydrogenation step, in which the anthraquinone compound in the working solution is hydrogenated in the presence of a catalyst to give the corresponding anthrahydroquinone compound.

Said catalytic hydrogenation can be carried out in suspension or in a fixed bed in various reactor types. The relevant prior art is described in detail in EP-A-0 672 617, for example. This reference relates to a process of the subject type using a fixed-bed reactor comprising a catalyst bed having an open structure. It is suggested to use palladium on a support, such as activated carbon, aluminum oxide or silica gel, as a catalyst.

EP-A-0 102 934 describes another version of the anthraquinone process which likewise utilizes a fixed bed having a structure containing specific, parallel passages. According to this reference, useful active metals for the catalysts described therein include noble metals, eg. palladium, platinum, rhodium or mixtures thereof.

U.S. Pat. No. 4,428,923 describes an anthraquinone process which is carried out in suspension and utilizes a loop reactor and palladium black as a catalyst.

EP-A-0 778 085 and WO 96/18574 describe the use of Pd, Rh, Pt or Ru as active metals in a catalyst suitable for the anthraquinone process, where conventional materials, such as $Al_2O_3$ or $SiO_2$, are used as support materials for the catalysts described.

The prior art catalysts did not always meet the requirements for such catalysts, such as a high activity together with a high selectivity. Furthermore, it was not always possible to achieve sufficiently high space-time yields.

It is an object of the present invention to provide novel processes for hydrogenating an anthraquinone compound using catalysts previously not used for said hydrogenation.

We have found that this object is achieved, in one embodiment, by a process for hydrogenating an anthraquinone compound or a mixture of two or more thereof by contacting the anthraquinone compound or the mixture of two or more thereof with a catalyst to obtain an anthrahydroquinone compound or a mixture of two or more thereof, which comprises using a catalyst (catalyst 1) comprising at least one homogeneous compound of at least one metal of transition group VIII of the Periodic Table of the Elements alone or together with at least one metal of transition group I or VII of the Periodic Table of the Elements, deposited on a support in situ.

The present invention further provides a process for hydrogenating an anthraquinone compound as described above, which comprises using a catalyst (catalyst 2) comprising, as active metal, at least one metal of transition group VIII of the Periodic Table of the Elements, alone or together with at least one metal of transition group I or VII of the Periodic Table of the Elements, applied to a support, the support having a mean pore diameter of at least 50 nm and a BET surface area of at most 30 $m^2/g$ and the amount of active metal being from 0.01 to 30% by weight, based on the total weight of the catalyst, and the ratio of the surface areas of the active metal and the catalyst support preferably being<0.05.

The invention further provides a process for hydrogenating an anthraquinone compound as defined above, which comprises using a catalyst (catalyst 3) comprising, as active metal, at least one metal of transition group VIII of the Periodic Table of the Elements, alone or together with at least one metal of transition group I or VII of the Periodic Table of the Elements, in an amount of from 0.01 to 30% by weight, based on the total weight of the catalyst, applied to a support, from 10 to 50% of the pore volume of the support being macropores having a pore diameter of from 50 nm to 10,000 nm and from 50 to 90% of the pore volume of the support being mesopores having a pore diameter of from 2 to 50 nm, the sum of the pore volumes being 100%.

In another embodiment, the present invention provides a process for hydrogenating an anthraquinone compound as described above, which comprises using a catal)-st (catalyst 4) comprising, as active metal, at least one metal of transition group VIII of the Periodic Table of the Elements with at least one metal of transition group I or VII of the Periodic Table of the Elements, in an amount of from 0.01 to 30% by weight, preferably from 0.2 to 15% by weight, based on the total weight of the catalyst, applied to a support, the support having a mean pore diameter of at least 0.1 ″m, preferably at least 0.5 ″m, and a surface area of at most 15 $m^2/g$, preferably at most 10 $m^2/g$.

The invention further provides a process for hydrogenating an anthraquinone compound as described above, which comprises using as a catalyst (catalyst 5) a monolithic supported catalyst obtainable by sequentially heating in air and cooling down a support material in the form of a metal fabric or metal foil, followed by coating with an active component under reduced pressure, subsequent cutting and shaping of the coated support material and finally processing to give a monolithic supported catalyst, using, as active metal, at least one metal of transition group VIII of the Periodic Table of the Elements alone or together with at least one metal of transition group I or VII of the Periodic Table of the Elements.

Any metal of transition group VIII of the Periodic Table of the Elements can in principle be used as active metal. Platinum, rhodium, palladium, cobalt, nickel or ruthenium or a mixture of two or more thereof are preferably used as active metals, in particular ruthenium. It is in principle likewise possible to use any metal of transition group I and/or VII, preference being given to using copper and/or rhenium.

For the purposes of the present invention, the terms "macropores" and "micropores" are used as defined in Pure Appl. Chem. 45 (1976) p. 79, namely to describe pores whose diameter is above 50 nm (macropores) or from 2 nm to 50 nm (mesopores).

The active metal content is generally from about 0.01 to about 30% by weight, preferably from about 0.01 to about 5% by weight, especially from about 0.1 to about 5% by weight, in each case based on the total weight of the catalyst used, the preferred contents of the catalysts 1 to 5 being specifically reported in the discussion of these catalysts.

"Anthraquinone compound" encompasses in principle all anthraquinone compounds and the corresponding tetrahydroanthraquinone compounds suitable for use in the preparation of hydrogen peroxide. The preferred compounds which can be used are described briefly in the chapter "Processing Procedure" below.

The catalysts 1 to 5 defined above will now be described in detail by way of example with reference to the use of ruthenium as active metal. The details given below also apply to the other active metals which can be used as defined herein.

CATALYST 1

The process of the invention can be carried out in the presence of a catalyst 1 comprising at least one homogeneous compound of at least one metal of transition group VIII of the Periodic Table of the Elements deposited on a support in situ, with or without at least one compound of at least one metal of transition group I or VII of the Periodic Table of the Elements. To prepare the catalysts, a homogeneous metal compound is co-fed into the reactor during the reaction together with the feed to be deposited on a support present in the reactor during the reaction.

It is also possible to introduce the homogeneous metal compound into the reactor prior to the reaction to be deposited on a support present in the reactor during a hydrogen treatment.

For the purposes of the present invention, "in situ" means that the catalyst is not prepared and dried separately and then fed into the reactor as a ready-to-use catalyst, but, according to the present invention, is formed in the reactor immediately before or during the actual hydrogenation.

For the purposes of the present invention, "homogeneous compound of a metal of transition group VIII, I or VII of the Periodic Table of the Elements" or "homogeneous ruthenium compound" means that the metal compound used according to the invention is soluble in the surrounding medium, ie. in the anthraquinone compound employed which is yet to be hydrogenated or in a mixture of these compounds with at least one solvent.

Useful metal compounds are in particular nitrosyl nitrates and nitrates, but also halides, carbonates, carboxylates, acetylacetonates, chloro complexes, nitrido complexes and amine complexes and also oxide hydrates or mixtures thereof. Preference is given to ruthenium nitrosyl nitrate, ruthenium(III) chloride, ruthenium(III) nitrate and ruthenium oxide hydrate.

Although there are no particular restrictions as to the amount of the metal compound applied to the carrier(s) in the process of the invention, in view of sufficient catalyst activity and process economy, the metal salt or metal complex is applied to the carrier in an amount sufficient to deposit from 0.01 to 30% by weight, based on the total weight of the catalyst, of active metal on the carrier(s). Said amount is more preferably from 0.2 to 15% by weight, particularly preferably about 0.5% by weight.

The supports present in the reactor are preferably metal meshes, metal rings and steatite bodies as described, among others, in EP-A-0 564 830 and EP-A-0 198 435. The supports particularly preferably used in the present invention and their preparation will nevertheless be described briefly below.

Particular preference is given to using metallic support materials, such as the stainless steels having the material numbers 1.4767, 1.4401, 2.4610, 1.4765, 1.4847, 1.4301, etc. since they can be surface-roughened by heat treatment before they are coated with active components. Particular preference is given to using Kanthal (material number 1.4767) or aluminum-containing metals as mesh materials. Kanthal is an alloy containing about 75% by weight Fe, about 20% by weight Cr and about 5% by weight Al. Heat treatment is effected by heating the metallic supports cited above in air at from 600 to 1100° C., preferably at from 800 to 1000° C., for from 1 to 20 hours, preferably for from 1 to 10 hours, and recooling. This pretreatment is crucial for the activity of the catalyst since it is virtually impossible to deposit ruthenium in situ on the metallic carriers without this heat treatment. After this treatment at elevated temperature, the support is coated with the ruthenium compound.

In a further preferred embodiment, the carriers described above may be coated by vapor deposition with a layer of a palladium metal, such as Ni, Pd, Pt, Rh, preferably Pd, having a thickness of from about 0.5 to about 10 nm, especially about 5 nm, as is likewise described in the abovementioned EP-A-0 564 830.

As can be seen from the examples according to the invention, a particular catalyst used as a support in the present invention is a mesh of heat-treated Kanthal onto which a Pd layer having a thickness of about 5 nm has been vapor-deposited to facilitate the deposition of the active metal.

It is, however, also possible to use conventional catalyst support systems, such as activated carbon, silicon carbide, aluminum oxide, silicon dioxide, titanium dioxide, zirconium dioxide, magnesium oxide, zinc oxide or mixtures thereof, in each case in the form of spheres, extrudates or rings. Among these, particular preference is given to aluminum oxide and zirconium dioxide. The pore size and the pore distribution are completely uncritical. It is possible to use bimodal supports or also any other type of support. The supports are preferably macroporous.

Catalyst 1 and its preparation are described in more detail in DE-A 196 22 705.4, the relevant contents of which are fully incorporated herein by reference.

CATALYST 2

The catalysts 2 used according to the present invention can be prepared industrially by applying at least one metal of transition group VIII of the Periodic Table of the Elements and, if desired, at least one metal of transition group I or VII of the Periodic Table of the Elements to a suitable support.

The application can be achieved by impregnating the support with aqueous metal salt solutions such as aqueous ruthenium salt solutions, by spraying appropriate metal salt solutions onto the support or by other suitable methods. Suitable metal salts of transition groups I, VII and VIII of the Periodic Table of the Elements are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts comprising not only a metal of transition group VIII of the Periodic Table of the Elements but also further metals as active metal on the support, the metal salts or metal salt solutions can be applied simultaneously or in succession.

The supports which have been coated or impregnated with the metal salt solution are then dried, preferably at from 100° C. to 150° C., and if desired calcined at from 200° C. to 600° C., preferably at from 350° C. to 450° C. In the case of separate impregnations, the catalyst is dried and if desired calcined, as described above, after each impregnation step. The order in which the active components are applied can be selected without restriction.

The coated, dried and if desired calcined supports are subsequently activated by treatment in a gas stream comprising free hydrogen at from about 30° C. to about 600° C., preferably from about 150° C. to about 450° C. The gas stream preferably comprises from 50 to 100% by volume of $H_2$ and from 0 to 50% by volume of $N_2$.

The metal salt solution(s) are applied to the support or supports in such an amount that the total active metal content, in each case based on the total weight of the catalyst, is from about 0.01 to about 30% by weight, preferably from about 0.01 to about 5% by weight, more preferably from about 0.01 to about 1% by weight, in particular from about 0.05 to about 1% by weight.

The total metal surface area on the catalyst is preferably from about 0.01 to about 10 $m^2/g$ of catalyst, more preferably from about 0.05 to about 5 $m^2/g$, in particular from about 0.05 to about 3 $m^2/g$. The metal surface area is determined by means of the chemisorption method described by J. LeMaitre et al. in "*Characterization of Heterogenous Catalysts*", eds. Francis Delanney, Marcel Dekker, New York 1984, pp. 310–324.

In the catalyst used according to the present invention, the ratio of the surface areas of the active metal/metals and the catalyst support is preferably less than about 0.05, the lower limit being about 0.0005.

The support materials which can be used for preparing the catalysts used according to the present invention are those which are macroporous and have a mean pore diameter of at least about 50 nm, preferably at least about 100 nm, in particular at least about 500 nm, and a BET surface area of at most about 30 $m^2/g$, preferably at most about 15 $m^2/g$, more preferably at most about 10 $m^2/g$, in particular at most about 5 $m^2/g$, even more preferably at most about 3 $m^2/g$. More precisely, the mean pore diameter of the support is preferably from about 100 nm to about 200 ″m, more preferably from about 500 nm to about 50″. The surface area of the support is preferably from about 0.2 to about 15 $m^2/g$, more preferably from about 0.5 to about 10 $m^2/g$, in particular from about 0.5 to about 5 $m^2/g$, even more preferably from about 0.5 to about 3 $m^2/g$.

The surface area of the support is determined by the BET method by $N_2$ adsorption, in particular in accordance with DIN 66131. The mean pore diameter and the pore size distribution are determined by Hg porosimetry, in particular in accordance with DIN 66133.

The pore size distribution of the support is preferably approximately bimodal, the bimodal pore diameter distribution having maxima at about 600 nm and about 20 ″m representing a specific embodiment of the invention.

Further preference is given to a support having a surface area of 1.75 $m^2/g$ and this bimodal pore diameter distribution. The pore volume of this preferred support is preferably about 0.53 ml/g.

Macroporous support materials which can be used are, for example, activated carbon, silicon carbide, aluminum oxide, silicon dioxide, titanium dioxide, zirconium dioxide, magnesium oxide, zinc oxide or mixtures of two or more of these, preference being given to using aluminum oxide and zirconium dioxide.

Catalyst 2 and its preparation are described in more detail in DE-A 196 24 484.6, the relevant contents of which are fully incorporated herein by reference.

CATALYST 3

The catalysts 3 used according to the present invention can be prepared industrially by applying an active metal of transition group VIII of the Periodic Table of the Elements, preferably ruthenium or palladium, and, if desired, at least one metal of transition group I or VII of the Periodic Table of the Elements to a suitable support. The application can be achieved by impregnating the support with aqueous metal salt solutions, such as ruthenium or palladium salt solutions, by spraying appropriate metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts comprising more than one active metal on the support, the metal salts or metal salt solutions can be applied simultaneously or in succession.

The supports which have been coated or impregnated with the metal salt solution are then dried, preferably at from 100° C. to 150° C., and if desired calcined at from 200° C. to 600° C., preferably at from 350° C. to 450° C. The coated supports are subsequently activated by treatment in a gas stream comprising free hydrogen at from 30° C. to 600° C., preferably from 100° C. to 450° C. and in particular from 100° C. to 300° C. The gas stream preferably comprises from 50 to 100% by volume of $H_2$ and from 0 to 50% by volume of $N_2$.

In the case of applying more than one active metal to the support and successive application, the support may be dried at from 100° C. to 150° C. and if desired calcined at from 200° C. to 600° C. after each application or impregnation step. The order in which the metal salt solutions are applied or impregnated can be selected without restriction.

The metal salt solution is applied to the support or supports in such an amount that the active metal content, in each case based on the total weight of the catalyst, is from 0.01 to 30% by weight, preferably from 0.01 to 10% by weight, further preferred from 0.01 to 5% by weight, in particular from 0.3 to 1% by weight.

The total metal surface area on the catalyst is preferably from 0.01 to 10 $m^2/g$ of catalyst, particularly preferably from about 0.05 to about 5 m²g, more preferably from about 0.05 to about 3 m²/g. The metal surface area was determined by means of the chemisorption method described by J. LeMaitre et al. in "Characterization of Heterogenous Catalysts", eds. Francis Delanney, Marcel Dekker, New York 1984, pp. 310–324.

In the catalyst used according to the present invention, the ratio of the surface areas of the at least one active metal and the catalyst support is less than about 0.3, preferably less than about 0.1, in particular about 0.05 or less, the lower limit being about 0.0005.

The support materials which can be used for the preparation of the catalysts used according to the invention have macropores and-mesopores.

The supports which can be used according to the invention have a pore distribution such that from about 5 to about 50%, preferably from about 10 to about 45%, more preferably from about 10 to 30%, in particular from 15 to 25%, of the pore volume are macropores having a pore diameter of from about 50 nm to about 10,000 nm and from about 50 to about 95%, preferably from about 55 to about 90%, more preferably from about 70 to about 90%, in particular from about 75 to about 85%, of the pore volume are mesopores having a pore diameter of from about 2 to about 50 nm, the sum of the pore volumes being 100% in each case.

The total pore volume of the support used according to the invention is from about 0.05 to about 1.5 cm³/g, preferably from about 0.1 to about 1.2 cm³/g and in particular about 0.3 to about 1.0 cm³/g. The mean pore diameter of the support used according to the invention is about 5 to about 20 nm, preferably about 8 to about 15 nm and in particular from about 9 to about 12 nm.

The surface area of the support is preferably from about 50 to about 500 m²/g of the support, more preferably from about 200 to about 350 m²/g, in particular from about 200 to about 250 m²/g.

The surface area of the support is determined by the BET method by $N_2$ adsorption, in particular in accordance with DIN 66131. The mean pore diameter and the pore size distribution are determined by Hg porosimetry, in particular in accordance with DIN 66133.

It is in principle possible to use any support material known in catalyst preparation, ie. having the pore size distribution defined above, but preference is given to activated carbon, silicon carbide, aluminum oxide, silicon dioxide, titanium dioxide, zirconium dioxide, magnesium oxide, zinc oxide or mixtures of two or more of these, further preference being given to using aluminum oxide and zirconium dioxide.

Catalyst 3 and its preparation are described in more detail in DE-A 196 24 485.4, the relevant contents of which are fully incorporated herein by reference.

CATALYST 4

The catalysts 4 used according to the present invention can be prepared industrially by applying an active metal of transition group VIII of the Periodic Table of the Elements and, if desired, at least one metal of transition group I or VII of the Periodic Table of the Elements to a suitable support. The application can be achieved by impregnating the support with aqueous metal salt solutions, such as ruthenium salt solutions, by spraying appropriate metal salt solutions onto the support or by other suitable methods. Suitable ruthenium salts for preparing the ruthenium salt solutions and also metal salts of transition groups I, VII and VIII of the Periodic Table of the Elements are the nitrates, nitrosyl nitrates, halides, carbonates, carboxylates, acetylacetonates, chloro complexes, nitrito complexes or amine complexes of the corresponding metals, preference being given to the nitrates and nitrosyl nitrates.

In the case of catalysts comprising more than one metal on the support, the metal salts or metal salt solutions can be applied simultaneously or in succession.

The supports which have been coated or impregnated with the ruthenium salt solution or metal salt solution are then dried, preferably at from 100° C. to 150° C., and if desired calcined at from 200° C. to 600° C.

The coated supports are subsequently activated by treatment in a gas stream comprising free hydrogen at from 30° C. to 600° C., preferably from 150° C. to 450° C. The gas stream preferably comprises from 50 to 100% by volume of $H_2$ and from 0 to 50% by volume of $N_2$.

If not only the active metal of transition group VIII of the Periodic Table of the Elements but also metals of transition group I or VII are applied to the support in succession, the support may be dried at from 100° C. to 150° C. and if desired calcined at from 200° C. to 600° C. after each application or impregnation step. The order in which the metal salt solutions are applied or impregnated can be selected without restriction.

The metal salt solution is applied to the support or supports in such an amount that the active metal content, in each case based on the total weight of the catalyst, is from 0.01 to 30% by weight, preferably from 0.2 to 15% by weight, particularly preferably about 0.5% by weight.

The total metal surface area on the catalyst is preferably from 0.01 to 10 m²/g of catalyst, more preferably from 0.05 to 5 m²/g, in particular from 0.05 to 3 m²/g.

The support materials which can be used for preparing the catalysts used according to the present invention are preferably those which are macroporous and have a mean pore diameter of at least about 0.1 ″m, preferably at least about 0.5 ″m, and a surface area of at most 15 m²/g, preferably at most 10 m²/g, particularly preferably at most 5 m²/g, in particular at most 3 m²/g. The mean pore diameter of the support is preferably from 0.1 to 200 ″m, in particular from 0.5 to 50 ″m. The surface area of the support is preferably from 0.2 to 15 m²/g, more preferably from 0.5 to 10 m²/g, in particular from 0.5 to 5 m²/g, especially from 0.5 to 3 m²/g.

The surface area of the support is determined by the BET method by $N_2$ adsorption, in particular in accordance with DIN 66131. The mean pore diameter and the pore size distribution are determined by Hg porosimetry, in particular in accordance with DIN 66133. The pore size distribution of the support may preferably be approximately bimodal, the bimodal pore diameter distribution having maxima at about 0.6 ″m and about 20 ″m representing a specific embodiment of the invention.

Particular preference is given to a support having a surface area of about 1.75 m²/g and this bimodal pore diameter distribution. The pore volume of this preferred support is preferably about 0.53 ml/g.

Macroporous support materials which can be used are, for example, activated carbon, silicon carbide, aluminum oxide, silicon dioxide, titanium dioxide, zirconium dioxide, magnesium oxide, zinc oxide or mixtures of two or more of these, preference being given to using aluminum oxide and zirconium dioxide.

Catalyst 4 and its preparation are described in more detail in DE-A 196 04 791.9, the relevant contents of which are fully incorporated herein by reference.

CATALYST 5

The catalyst 5 used according to the invention can be prepared by sequentially heating in air and cooling down of a support material in the form of a metal fabric or metal foil, followed by coating with the above-described active metal or a combination of two or more thereof under reduced pressure, subsequent cutting and shaping of the coated support material and finally processing to give a monolithic catalyst element. This catalyst and its preparation are described in more detail in EP-A-0 564 830 and U.S. Pat. No. 4,686,202, the relevant contents of which are fully incorporated herein by reference. The essential features of the preparation of this catalyst and its preferred embodiments will herein only be discussed briefly. What was said regarding the active metals used for catalysts 1 to 4 also applies here.

Particularly suitable examples of metallic support materials in the form of metal foils or metal fabrics are stainless steels, for example those having the material numbers 1.4767, 1.4401, 2.4610, 1.4765, 1.4847, 1.4301, etc. since they can be surface-roughened by heat treatment before they are coated with active components. To this end, the metallic supports are heated in air at from 600 to 1100° C., preferably at from 800 to 1000° C., for from 1 to 20 hours, preferably for from 1 to 10 hours, and then recooled. This pretreatment is crucial for the activity of the catalyst. After this treatment at elevated temperature, the support is coated with the active component. To this end, the support is coated simultaneously or successively, batchwise or continuously, with the active components under a reduced pressure of from $10^{-3}$ to 10–5 mbar by means of an evaporation unit, for example electron beam evaporation, or a sputtering unit. This can be followed by heat treatment under an inert gas or air in order to activate the catalyst.

The aim of the preparation of catalyst layers described here is to prepare highly unordered and defective polycrystalline layers or clusters. It is therefore normally not necessary for the vacuum conditions to be particularly good. Furthermore, alternate deposition of active components and structural promoters allows the active components to be produced in very finely crystalline or cluster-like form.

Here, the catalyst can be built up systematically, for example in a vapor deposition unit containing a plurality of different evaporation sources. Thus, for example, it is possible first to apply an oxide layer or, by reactive evaporation, an adhesive layer to the support. Active components and promoters can be prepared on this base layer in a plurality of alternate layers. By admitting a reactive gas into the recipient, promoter layers of oxides or other compounds can be produced. Interim heat treatment can also be carried out.

Due to this method of production of the catalyst fabric or catalyst foils, the active components have such high adhesion that they can be cut, shaped and processed to give monolithic catalyst elements.

A very simple monolithic catalyst is obtained if the catalyst fabric or catalyst foil is shaped by ring gear rolling and flat and corrugated fabric or foil is rolled up to form a cylindrical monolith having identical vertical channels. However, it is also possible to shape any desired static mixers from this catalyst material, since the adhesion of the catalyst layer is sufficiently high.

The monolithic catalyst elements produced in this way, in the form of mixed elements, are installed in a reactor and charged with the reaction liquid to be reacted.

PROCESSING PROCEDURE

In the process of the invention, the hydrogenation is generally carried out at from about 20 to 120° C., preferably from about 30 to 80° C., pressures employed being usually from about 1 to about 20 bar, preferably from about 2 to 10 bar.

The hydrogenation can be carried out with pure hydrogen or a hydrogen-containing gas.

To achieve a very high selectivity of generally >90%, preferably >95%, the hydrogenation is usually allowed to proceed until a conversion of about 50 to 70% is reached.

Preferred anthraquinone compounds used according to the invention are 2-alkylanthraquinones, such as 2-ethyl-, 2-tert-butyl, 2-amyl-, 2-methyl-, 2-butyl-, 2-isopropyl-, 2-sec-butyl-, 2-sec-amylanthraquinone, and polyalkylanthraquinones, such as 1,3-diethylanthraquinone, 2,3-dimethylanthraquinone, 1,4-dimethylanthraquinone, 2,7-dimethylanthraquinone, and the corresponding tetrahydroanthraquinone compounds and mixtures of two or more thereof.

Any solvent known in the prior art as a solvent for anthraquinone or anthrahydroquinone compounds may be used. Preference is given to mixtures of two or more solvent components since such solvent mixtures provide an optimum balance for the different solubility characteristics of anthraquinone and anthrahydroquinone compounds. Examples include mixtures of methylnaphthalene and nonyl alcohol, methylnaphthalene and tetrabutylurea, polyalkylated benzene and alkylphosphates or methylnaphthalene, tetrabutylurea and alkylphosphates.

Nor are there any restrictions on the reactors which can be used in the process of the invention so that all reactors known from the prior art and suitable for hydrogenations may be used.

The present invention further provides a process for preparing hydrogen peroxide by the anthraquinone process, which comprises the following steps (1) and (2):

(1) hydrogenating an anthraquinone compound or a mixture of two or more thereof by a process as defined above to obtain an anthrahydroquinone compound or a mixture of two or more thereof, and (2) reacting the anthraquinone compound or the mixture of two or more thereof with an oxygen-containing gas to give a mixture comprising hydrogen peroxide and the anthraquinone compound or the mixture of two or more thereof.

The steps (1) and (2) are preferably conducted continuously, more preferably continuously with recycling of the anthraquinone compound obtained in step (2) to step (1), the anthraquinone compound being recycled after removal of the hydrogen peroxide formed as a constituent of a working solution.

In a further embodiment of the process of the invention, the hydrogen peroxide is extracted in a further step (3) using an aqueous extractant, preference being given to using pure water.

As regards general procedures for conducting the anthraquinone process comprising the steps (1) to (3) above, reference is made to the prior art mentioned at the beginning.

The examples which follow illustrate the invention.

EXAMPLES

Example 1

A mesh of 1 mm mesh diameter made of heat-treated Kanthal onto which a Pd layer having a thickness of 5 nm had been vapor-deposited was placed in a 3.5 l autoclave. A Comparative Example indicated that this Pd-coated mesh was not catalytically active. In the first run, the autoclave was charged with 2 l of a 13% strength solution of 2-ethylanthraquinone in a 70:30 mixture of Shellsol® and tetrabutylurea together with 200 mg of ruthenium nitrosyl nitrate.

The batch was then hydrogenated at a hydrogen pressure of 10 bar for 60 minutes. The reaction effluent contained no ruthenium. 2-Ethylanthraquinone was converted to 2-ethylanthrahydroquinone at a selectivity of 100% (conversion: 72%). In the second run, 2 l of this solution were converted with hydrogen over the mesh catalyst without added ruthenium in the same manner.

The reaction effluent contained no traces of ruthenium. 75% of the 2-ethylanthraquinone were converted (selectivity: 100%).

Example 2

A stainless steel fabric (material number 1.4767) was heated in air at 900° C. for 5 h in a muffle furnace. The fabric thus obtained was ring gear rolled and the corrugated piece of fabric was then rolled up with a flat piece of fabric. The monolith thus obtained was precisely fitted into a continuous 0.3 l hydrogenation reactor.

2 g of ruthenium nitrosyl nitrate were dissolved in 500 ml of a 70:30 Shell-sol® /tetrabutylurea mixture. This solution was continuously metered into the reactor in an amount of 60 ml/h at a hydrogen pressure of 10 bar and at 100° C. The reaction effluent obtained was colorless and contained no ruthenium. After addition of the ruthenium-containing solution was complete, the working solution (13% of 2-ethylanthraquinone in a 70:30 mixture of Shellsol®/ tetrabutylurea) was continuously metered into the reactor in an amount of 300 ml/h at a hydrogen pressure of 10 bar and at 40° C. without addition of ruthenium.

The conversion was 62% and the selectivity was 100%, based on 2-ethylanthrahydroquinone, as determined by gas chromatography.

We claim:

1. A process for hydrogenating an anthraquinone compound or a mixture of anthraquinone compounds by contacting the anthraquinone compound or mixture of anthraquinone compounds with a catalyst and pure hydrogen or a hydrogen containing gas thereby preparing an anthrahydroquinone compound or a mixture of anthrahydroquinone compounds, which comprises:

effecting said contact with a catalyst comprising at least one homogeneous compound of at least one metal of transition metal Group VIII of the Periodic Table of the Elements deposited alone or together with at least one metal of transition Group I or VII of the Periodic Table of the Elements on a support in situ.

2. A process for hydrogenating an anthraquinone compound or a mixture of anthraquinone compounds by contacting the anthraquinone compound or mixture of anthraquinone compounds with a catalyst and pure hydrogen or a hydrogen containing gas thereby preparing an anthrahydroquinone compound or a mixture of anthrahydroquinone compounds, which comprises:

effecting said contact with a catalyst comprising, as active metal, at least one metal of transition Group VIII of the Periodic Table of the Elements, except palladium, alone or together with at least one metal of transition Group I or VII of the Elements, applied to a support, the support having a mean pore diameter of at least 50 nm and a BET surface area of at most 30 m$^2$/g and the amount of active metal being from 0.01 to 30% by weight, based on the total weight of the catalyst.

3. A process for hydrogenating an anthraquinone compound or a mixture of anthraquinone compounds by contacting the anthraquinone compound or mixture of anthraquinone compounds with a catalyst and pure hydrogen or a hydrogen containing gas thereby preparing an anthrahydroquinone compound or a mixture of anthrahydroquinone compounds, which comprises:

effecting said contact with a catalyst comprising, as active metal, ruthenium, alone or together with at least one metal of transition Group I or VII of the Elements, in an amount ranging from 0.01 to 30% by weight, based on the total weight of the catalyst, applied to a support, from 10 to 50% of the pore volume of the support being macropores having a pore diameter ranging from 50 nm to 10,000 nm and from 50 to 90% of the pore volume of the support being mesopores having a pore diameter ranging from 2 to 50 nm, the sum of the pore volumes being 100%.

4. A process for hydrogenating an anthraquinone compound or a mixture of anthraquinone compounds by contacting the anthraquinone compound or mixture of anthraquinone compounds with a catalyst and pure hydrogen or a hydrogen containing gas thereby preparing an anthrahydroquinone compound or a mixture of anthrahydroquinone compounds, which comprises:

effecting said contact with a catalyst comprising, as active metal, at least one metal of transition Group VIII of the Periodic Table of the Elements, alone or together with at least one metal of transition Group I or VII of the Periodic Table of the Elements, in an amount ranging from 0.01 to 30% by weight, based on the total weight of the catalyst, applied to a support, the support having a pore diameter at least 0.1 µm and a BET surface area of at most 15m$^2$/g.

5. A process for hydrogenating an anthraquinone compound or a mixture of anthraquinone compounds by contacting the anthraquinone compound or mixture of anthraquinone compounds with a catalyst and pure hydrogen or a hydrogen containing gas thereby preparing an anthrahydroquinone compound or a mixture of anthrahydroquinone compounds, which comprises:

effecting said contact with a catalyst supported on a monolithic support of a metal fabric or a metal foil prepared by sequentially heating said support material in air and then cooling the support material, followed by coating the support material with an active component under reduced pressure, and subsequently cutting and shaping the coated support material and finally processing to give a monolithic supported catalyst, whose active metal is at least one metal of transition Group VIII of the Periodic Table of the Elements, alone or together with at least one metal of transition Group I or VII of the Periodic Table of the Elements.

6. A process for preparing hydrogen peroxide by the anthraquinone process, which comprises:

(1) hydrogenating an anthraquinone compound or a mixture of anthraquinone compounds by a process as claimed in any one of claims 1, 2, 3, 4 and 5 thereby preparing an anthrahydroquinone compound or a mixture of anthrahydroquinone compounds; and (2) reacting the anthrahydroquinone compound or said mixture of anthrahydroquinone compounds with an oxygen-containing gas to give a mixture comprising hydrogen peroxide and the anthraquinone compound or said mixture of anthraquinone compounds.

7. A process as claimed in claim 6, wherein the steps (1) and (2) are carried out continuously.

8. A process as claimed in claim 6, which further comprises (3) extracting the hydrogen peroxide from the mixture comprising hydrogen peroxide and the anthraquinone compound or said mixture of anthraquinone compounds with an aqueous extractant.

9. A process as claimed in claim 7, which further comprises:

(3) extracting the hydrogen peroxide from the mixture comprising hydrogen peroxide and the anthraquinone compound or said mixture of anthraquinone compounds with an aqueous extractant.

10. The process as claimed in claim 1, wherein a 2-alkylanthraquinone or a mixture of 2-alkylanthraquinone compounds is the anthraquinone starting material.

11. The process as claimed in claim 2, wherein a 2-alkylanthraquinone or a mixture of 2-alkylanthraquinone compounds is the anthraquinone starting material.

12. The process as claimed in claim 3, wherein a 2-alkylanthraquinone or a mixture of 2-alkylanthraquinone compounds is the anthraquinone starting material.

13. The process as claimed in claim 4, wherein a 2-alkylanthraquinone or a mixture of 2-alkylanthraquinone compounds is the anthraquinone starting material.

14. The process as claimed in claim 5, wherein a 2-alkylanthraquinone or a mixture of 2-alkylanthraquinone compounds is the anthraquinone starting material.

15. The process as claimed in claim 6, wherein a 2-alkylanthraquinone or a mixture of 2-alkylanthraquinone compounds is the anthraquinone starting material.

16. The process as claimed in claim 3, wherein from 10 to 45% of the pore volume of the support exists as macropores and from 55 to 90% of the pore volume exists as mesopores.

17. The process as claimed in claim 16, wherein from 10 to 30% of the pore volume of the support exists as macropores and from 70 to 90% of the pore volume exists as mesopores.

18. The process as claimed in claim 16, wherein from 15 to 25% of the pore volume of the support exists as macropores and from 75 to 85% of the pore volume exists as mesopores.

* * * * *

UNITED STATES PATENT AND TRADEMARK OFFICE
CERTIFICATE OF CORRECTION

PATENT NO. : 6,464,954 B2
DATED : October 15, 2002
INVENTOR(S) : Boettcher et al.

It is certified that error appears in the above-identified patent and that said Letters Patent is hereby corrected as shown below:

<u>Title page,</u>
Item [45], and the Notice information should read as follows:

-- [45] **Date of Patent: \*Oct. 15, 2002**
  [\*] Notice: This patent issued on a continued prosecution application filed under 37 CFR 1.53(d), and is subject to the twenty year patent term provisions of 35 U.S.C 154(a)(2).

Subject to any disclaimer, the term of this patent is extended or adjusted under 35 U.S.C. 154(b) by 0 days. --

Signed and Sealed this

Eleventh Day of February, 2003

JAMES E. ROGAN
*Director of the United States Patent and Trademark Office*